(12) United States Patent
Palmer et al.

(10) Patent No.: US 6,461,310 B1
(45) Date of Patent: *Oct. 8, 2002

(54) ENDOSCOPIC BIOPTOME WITH A HARD STOP TO CONTROL BITING FORCE

(76) Inventors: Matthew A. Palmer, 7220 SW. 110 Ter., Miami, FL (US) 33156; Vincent Turturro, 1860 SW. 137 Way, Miramar, FL (US) 33027

( * ) Notice: Subject to any disclaimer, the term of this patent is extended or adjusted under 35 U.S.C. 154(b) by 3 days.

This patent is subject to a terminal disclaimer.

(21) Appl. No.: 09/612,923

(22) Filed: Jul. 10, 2000

Related U.S. Application Data (62) Division of application No. 08/960,214, filed on Oct. 29, 1997.

(51) Int. Cl.[7] .................................................. A61B 5/00
(52) U.S. Cl. ...................................... 600/567; 606/205
(58) Field of Search ................................. 600/562, 564; 606/205, 206, 207, 208, 209

(56) References Cited

U.S. PATENT DOCUMENTS

| | | |
|---|---|---|
| 3,989,033 A | 11/1976 | Halpern et al. |
| 4,522,206 A | 6/1985 | Whipple et al. |
| 4,651,752 A | 3/1987 | Fuerst |
| 4,815,476 A | 3/1989 | Clossick |
| 4,887,612 A | 12/1989 | Esser et al. |
| 4,896,678 A | 1/1990 | Ogawa |
| 5,052,402 A | 10/1991 | Bencini et al. |
| 5,171,255 A | 12/1992 | Rydell |
| 5,222,973 A | 6/1993 | Sharpe et al. |
| 5,318,589 A | 6/1994 | Lichtman |
| 5,636,639 A | 6/1997 | Turturro et al. ............. 128/751 |
| 5,746,216 A | 5/1998 | Turturro et al. ............. 128/751 |
| 6,123,678 A * | 9/2000 | Palmer et al. .............. 600/567 |
| 6,193,671 B1 | 2/2001 | Turturro et al. ............. 600/564 |

* cited by examiner

Primary Examiner—Kevin Shaver
Assistant Examiner—Pamela Wingood (57) ABSTRACT

An endoscopic bioptome includes a flexible coil having a lumen with an axially displaceable wire extending therethrough. The proximal ends of coil and wire couple to a manual actuator for axially displacing one of the coil and wire relative to the other. The distal end of the coil couples to either a jaw assembly or a cylinder. The jaw assembly includes a pair of jaws each having a distal jaw cup having a proximal neck and a relatively narrow bent resilient arm. The distal end of the wire couples to the other of the cylinder or the jaw assembly. The cylinder is slidable over the jaw assembly. Axial movement of either the wire relative to the coil or vice versa moves the cylinder over the arms of the jaws and over the necks of the jaw cups, thereby forcing the jaw cups together in a biting action.

11 Claims, 3 Drawing Sheets

ENDOSCOPIC BIOPTOME WITH A HARD STOP TO CONTROL BITING FORCE

This is a division of application Ser. No. 08/960,214, filed Oct. 29, 1997, incorporated herein by reference.

This application is related to co-owned U.S. application Ser. No. 08/189,937 filed Feb. 1, 1994, co-owned U.S. Ser. No. 08/584,801 filed Jan. 11, 1996, co-owned U.S. Ser. No. 08/440,326 filed May 12, 1995, and co-owned U.S. Ser. No. 08/412,058 filed Mar. 28, 1995, each of which is hereby incorporated by reference herein in its entirety.

BACKGROUND OF THE INVENTION

1. Field of the Invention

This invention relates to endoscopic surgical instruments. More particularly, this invention relates to an instrument for taking biopsy tissue samples.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and U.S. Pat. No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that suctioning tissue samples through a long narrow flexible bioptome is extremely difficult and fraught with problems.

Efforts have been made to provide a multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade far moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

Related application Ser. No. 08/189,937 discloses an endoscopic multiple sample bioptome having a hollow outer member and an axially displaceable inner member extending therethrough. The proximal ends of the outer and inner members are coupled to an actuator for axially displacing one relative to the other. The distal end of the outer member is coupled to one of a cylinder having a sharp distal edge and a jaw assembly, while the distal end of the inner member is coupled to the other. The jaw assembly includes a pair of opposed, preferably toothed, jaw cups each of which is coupled by a resilient arm to a base member. The resilient arms are bent to urge the jaws away from each other. The base member is mounted inside the cylinder and axial movement of the jaw assembly and cylinder relative to each other draws the resilient arms into the cylinder and brings the jaw cups together in a biting action. Depending on the geometry of the resilient arms, however, when the cylinder is moved over the arms, they may tend to bow inward and prevent a complete closing of the jaws. This results in a less than optimal biting action.

Related application Ser. No. 08/412,058 discloses an endoscopic multiple sample bioptome having enhanced biting action where the biting force at the jaws is substantially increased. In some cases, however, too much biting force at the jaws may be undesirable.

SUMMARY OF THE INVENTION

It is therefore an object of the invention to provide an endoscopic bioptome which has controlled jaw engagement and biting force.

It is also an object of the invention to provide an endoscopic multiple sample bioptome of controlled jaw engagement and biting force which is easy to operate.

In accord with these objects which will be discussed in detail below, the endoscopic bioptome of the present invention includes a relatively long flexible coil having a lumen with an axially displaceable wire extending therethrough. The proximal ends of the flexible coil and wire are coupled to a manual actuation means for axially displacing one of the flexible coil and wire relative to the other. According to a first embodiment of the invention, the distal end of the flexible coil is coupled to a jaw assembly and the distal end of the wire is coupled to a cylinder which is slidable over the jaw assembly. The wire is also provided near the distal end with a coaxial stopping band. The jaw assembly includes a pair of jaws each having a distal jaw cup having a proximal neck and a relatively narrow bent resilient mounting arm. The mounting arm of each jaw is coupled to the distal end of the coil by a washer (or retaining sleeve) through which a hollow threaded screw is threaded into the coil. The distal end of the wire extends through the hollow threaded screw and is coupled to the cylinder which is slidable over the jaw assembly. Axial movement of the wire relative to the coil moves the cylinder over the bent resilient arms of the jaws and over the necks of the jaw cups, thereby forcing the jaw cups together in a biting action. However, axial movement of the wire is limited by the coaxial stopping band which is arranged to abut the hollow screw as soon as the jaws close. The distance between the stopping band and the proximal end of the hollow screw is preferably equal to the distance between the distal end of the cylinder and the point on the jaw cups where the distal end of the cylinder lies when the jaws are closed.

According to a second embodiment of the invention, the distal end of the coil is coupled to a cylinder and the distal end of the wire is coupled to a jaw assembly which is slidable into and out of the cylinder. The jaw assembly includes a pair of opposed jaw cups, each of which is coupled by a narrow arm to a base member which resides inside the cylinder. The narrow arm of each jaw is a resilient member which includes a portion which is bent away from the longitudinal axis of the cylinder in order to locate the jaw cups substantially apart from each other. Axial movement of one of the jaw assembly and cylinder relative to the other draws the arms of the jaws into the cylinder or moves the cylinder over the arms of the jaws to bring the jaw cups together in a biting action.

In accord with the second embodiment of the invention, the cylinder is provided with an annular stopping crimp which prevents further proximal movement of the jaw assembly (or distal movement of the cylinder) once the jaws have closed. The distance between the stopping crimp and the proximal end of the jaw assembly is preferably equal to the distance between the distal end of the cylinder and the point on the jaw cups where the distal end of the cylinder lies when the jaws are closed.

According to a third embodiment of the invention, the distal end of the coil is coupled to a jaw assembly and the distal end of the wire is coupled to a cylinder which is slidable over the jaw assembly. The jaw assembly includes a pair of jaws each having a distal jaw cup having a proximal neck and a relatively narrow bent resilient mounting arm. The mounting arm of each jaw is coupled to the distal end of the coil by a washer (or retaining sleeve) through which a hollow threaded screw is threaded into the coil. The distal end of the wire extends through the hollow threaded screw and is coupled to the cylinder which is slidable over the jaw assembly. Axial movement of the wire relative to the coil moves the cylinder over the bent resilient arms of the jaws and over the necks of the jaw cups, thereby forcing the jaw cups together in a biting action.

In accord with the third embodiment of the invention, a portion of the coil adjacent to the jaw assembly is ground to a reduced diameter and the cylinder is provided with a radially inward flange. Axial movement of the cylinder is limited by the flange which abuts the washer (or retaining sleeve) of the jaw assembly as soon as the jaws close.

According to a fourth embodiment of the invention, each jaw cup is provided a step on its outer surface which limits distal movement of the cylinder and/or proximal movement of the jaw assembly as soon as the jaws close.

Additional objects and advantages of the invention will become apparent to those skilled in the art upon reference to the detailed description taken in conjunction with the provided figures.

DETAILED DESCRIPTION OF THE PREFERRED EMBODIMENTS

Referring now to FIGS. 1 through 4, a multiple sample bioptome 10 according to the invention includes a proximal handle 12 and a distal end effector 14. A long flexible coil 16 having an axially displaceable control wire 18 extending therethrough couples the handle 12 and the end effector 14. The coil 16 is preferably covered with a PTFE, FEP or polyolefin sheath 15 along substantially all of its length and a strain relief sleeve 17 covering a portion of the coil which extends from the handle 12. The control wire 18 is preferably flexible but longitudinally inelastic and is ideally formed from 304 Steel and provided with and outer diameter of approximately 0.018 inch. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a central through hole 32 and a radially engaging set screw 34. A short bore 36 and a radially engaging set screw 38 are provided in the shaft 20 distal of the thumb ring 24 with the bore 36 communicating with the longitudinal slot 28. The proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effector 14 as described in detail below.

Figure 2:
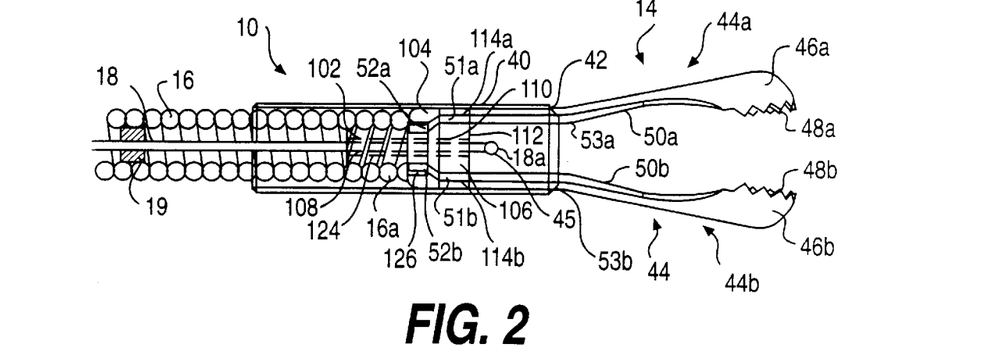
FIG. 2 is an enlarged partially transparent side elevation view of the distal end of a first embodiment of a bioptome of the invention with the jaws open.
Figure 3:
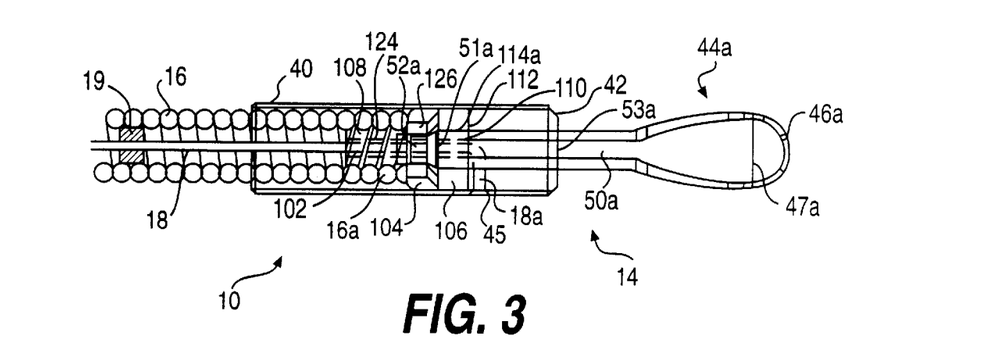
FIG. 3 is an enlarged transparent top view of the distal end of the bioptome of FIG. 2 with the jaws open.
Figure 4:
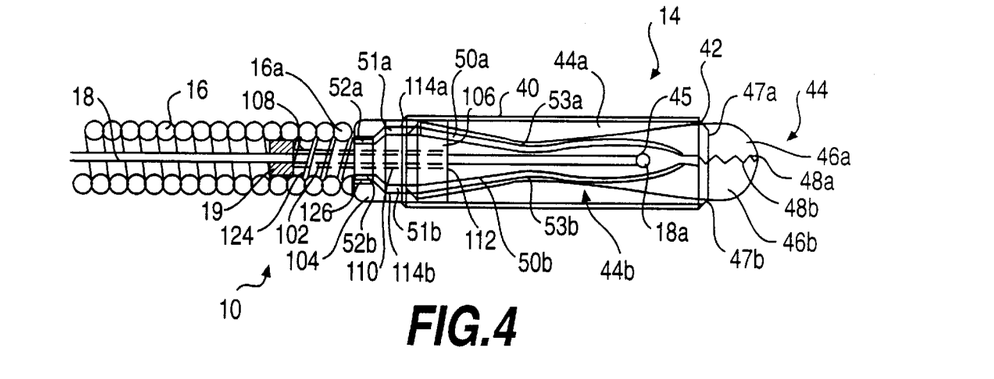
FIG. 4 is a view similar to FIG. 2, but with the jaws closed.

Turning now to FIGS. 2 through 4, according to a first embodiment of the invention, the end effector 14 includes a cylinder 40 having a distal edge 42 and a jaw assembly 44. The jaw assembly 44 includes a pair of end effectors 44a, 44b, a screw 102, and a washer or retaining sleeve 104. Each end effector 44a, 44b includes a jaw cup 46a, 46b preferably having a rim 48a, 48b with radially arranged teeth, and a resilient, preferably narrow, arm 50a, 50b which extends proximally from the jaw cup 46a, 46b. The proximal end 51a, 51b of the narrow arm 50a, 50b preferably includes a sharply descending angled portion 52a, 52b. The approximate center of the arm 50a, 50b is bent at 53a, 53b so that the arms diverge as seen in FIG. 2. The arms 50a, 50b are formed from super-elastic memory metal such as Nitinol (nickel-titanium alloy), and are biased apart from each other due to bends 53a, 53b, thereby urging the jaw cups 46a, 46b apart as seen in FIG. 2. In addition, as the arms 50a, 50b and the jaws 46a, 46b are preferably integral with each other, the jaws are preferably formed from a super-elastic or shape memory metal.

The proximal end 51a, 51b of each arm 50a, 50b is coupled to the distal end 16a of the coil 16 by crimping/locking with a hollow threaded screw 102 and a washer 104. The threaded screw 102 is substantially cylindrical, and generally includes a head portion 106, a threaded portion 108, and a cylindrical throughbore 110 along its central axis. The throughbore 110 is dimensioned to receive and allow movement of the control wire 18. The distal end 112 of the head portion 106 has a diameter substantially equal to that of the outer diameter of the coil 16, and is provided with two opposing grooves 114a, 114b on the outer perimeter of the distal end 112 of the head portion 106. Grooves 114a, 114b are dimensioned to receive the angled portion 52a, 52b at the proximal end 51a, 51b of each of the narrow arms 50a, 50b. The proximal end of the head portion 106 is frustroconical with a smaller diameter at the threaded portion 108. The threaded portion 108 has a diameter slightly larger than the inner diameter of the coil 16 and the proximal end of the threaded portion 108 includes threads 124 for lockingly engaging the interior of the distal end 16a of the coil 16.

The washer 104 is substantially cylindrical, and generally includes a throughbore 126. The distal portion of the throughbore 126 is frustroconical. It will be appreciated that the throughbore 126 of the washer 104 has substantially the same configuration as the proximal end of the head portion 106 of the screw 102. It will therefore be understood that the throughbore 126 of the washer 104 is dimensioned for engaging the proximal end of the head portion 106 of the screw 102 and distal end 16a of the coil 16 with the stepped 52a, 52b proximal ends 51a, 51b of the narrow arms 50a, 50b positioned in the grooves 114a–b of the threaded screw 102 when the screw is threaded into the interior of the distal end 16a of the coil 16. The stepped 52a, 52b proximal ends 51a, 51b of the narrow arms 50a, 50b are thus fastened between the washer 104 and the threaded screw 102.

As shown in FIGS. 2 through 4, the control wire 18 is provided with a bent end 18a which is welded to a hole 45 in the side of the cylinder 40. However, as described in detail in the related applications, other methods of coupling the control wire to the cylinder are possible. The cylinder 40 is slidably mounted over the cylindrical washer 104 and head portion 106 of the threaded screw 102, and is axially movable over the resilient arms 50a, 50b, thereby bending the arms and closing the jaws 46a, 46b as shown in FIG. 4. As the resilient arms 50a, 50b are made of superelastic metal, they will immediately return to their original open position (FIG. 2) once the cylinder 40 is retracted.

As seen best in FIGS. 3 and 4, each jaw 46a, 46b has a widest part or apex 47a, 47b which is denoted by the line 47a in FIG. 3. When the distal end 42 of the cylinder 40 reaches the apex 47a, 47b of the jaws (or some definite point proximal of the apex), the jaws are completely closed.

Figure 5:
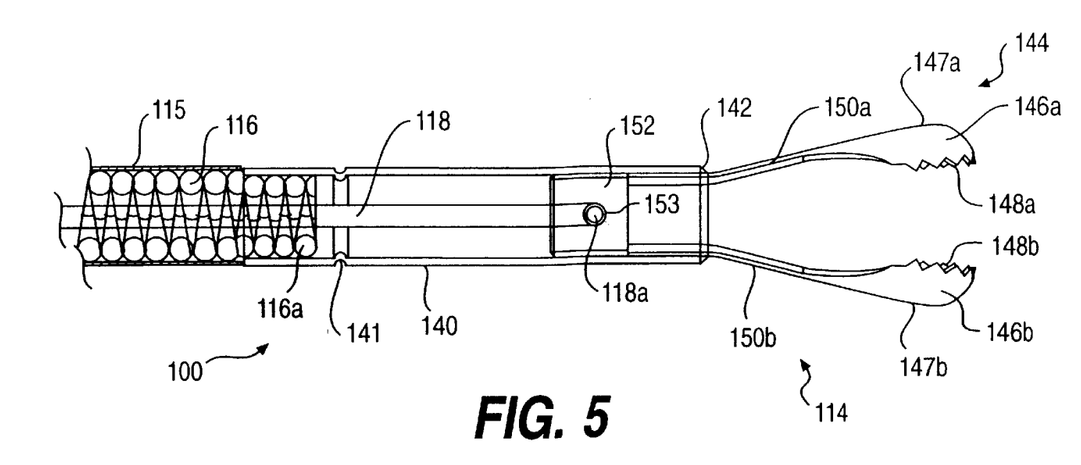
FIG. 5 is a view similar to FIG. 2 of a second embodiment of the invention.

From the foregoing description and with reference to FIGS. 1 through 4, those skilled in the art will appreciate that when the spool 22 and the shaft 20 are axially displaced relative to each other, the cylindrical sleeve 40 and the end effectors 44a, 44b are similarly axially displaced relative to each other, from the positions shown in FIG. 2 to the positions shown in FIG. 5 and vice versa. When the spool 22 and shaft 20 are in the approximate position shown in FIG. 1, the cylindrical sleeve 40 and the end effectors 44a, 44b will be in the approximate position shown in FIG. 2; i.e., with the jaws open. Thus, when the spool 22 is moved towards the thumb ring 24, or vice-versa, the cylindrical sleeve 40 and the end effectors 44a, 44b will be brought into the approximate position shown in FIG. 4; i.e., with the jaws closed. Moreover, it will also be appreciated that it is preferable to move the thumb ring 24 relative to the spool 22, rather than vice versa since that will move the cylindrical sleeve 40 relative to the end effectors 44*a*, 44*b* rather than vice versa. This is desirable so that the end effectors are not moved away from a tissue sample while the jaws are being closed.

According to the first embodiment of the invention, a crimped stopping band or welded stopping sleeve 19 is provided on the control wire 18. The stopping band 19 has an outer diameter which is larger than the diameter of the throughbore 110 of the screw 102. The stopping band 19 is specifically located on the control wire 18 so that the distance between the stopping band 19 and the screw 102 is substantially equal to the distance between the distal edge 42 of the cylinder 40 and the apices 47*a*, 47*b* (or desired closing point) of the jaws 46*a*, 46*b*. Therefore, when the jaws are moved to the closed position as shown in FIG. 4, the control wire 18 and the coil 16 are stopped from further displacement by the stopping band 19 and the screw 102. The hard stop provided by the stopping band 19 abutting the screw 102 prevents the cylinder 40 from pushing harder on the end effectors.

Figure 1:
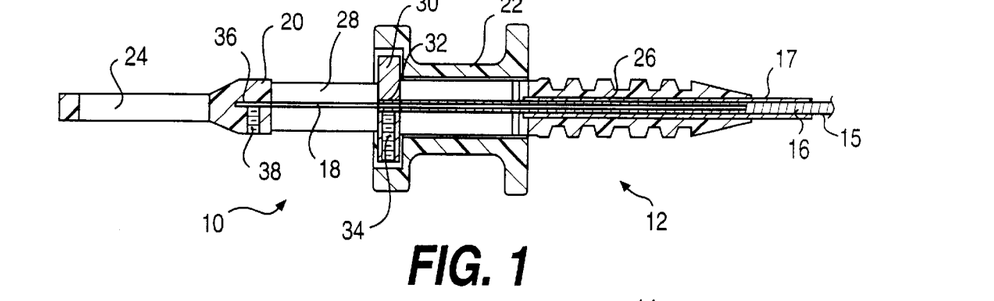
FIG. 1 is a side elevation view in partial section of the proximal end of a bioptome according to the invention.
Figure 6:
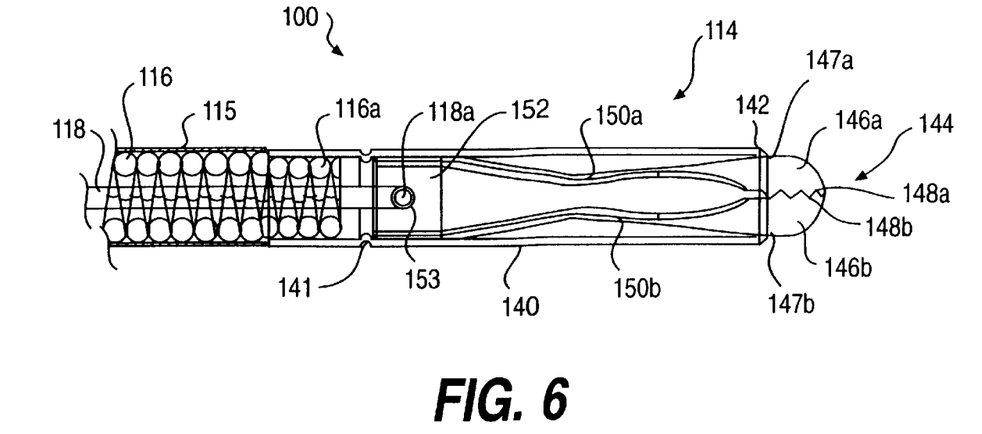
FIG. 6 is a view similar to FIG. 4 of the second embodiment of the invention.

Turning now to FIGS. 5 and 6, and with reference to FIG. 1, a second embodiment of a bioptome 100 according to the invention may utilize substantially the same proximal handle 12 as the bioptome 10 described above. The difference in this second embodiment lies primarily in the end effector assembly 114 and in how that assembly is coupled to a coil 116 and control wire 118. The coil 116 may be substantially the same as the coil 16 described above, having a sheath 115, and the control wire 118 may be substantially the same as the control wire 18 described above, having a bent end 118*a*. According to this second embodiment of the invention, the end effector 114 includes a cylinder 140 having a distal edge 142, and a jaw assembly 144. The jaw assembly 144 includes a pair of opposed jaw cups 146*a*, 146*b* each preferably having a plurality of sharp teeth 148*a*, 148*b*. A resilient, preferably narrow, arm 150*a*, 150*b* extends proximally from each jaw cup 146*a*, 146*b*. A cylindrical base member 152 joins the proximal ends of the arms 150*a*, 150*b*. The narrow resilient arms 150*a*, 150*b* are biased apart from each other, thereby urging the jaw cups 146*a*, 146*b* apart. The cylindrical base member 152 of the jaw assembly 144 is coupled to the distal end 118*a* of the control wire 118 by providing the base member 152 with a lateral hole 153 and providing the distal end 118*a* of the control wire with a substantially right angle bend. The distal end 118*a* of the control wire 118 is soldered or otherwise attached in the hole 153 in the base member 152. The cylinder 140 is coupled to the distal end 116*a* of the coil 116 by crimping and/or soldering.

From the foregoing description, and with reference to FIGS. 1, 5, and 6, those skilled in the art will appreciate that when the spool and the shaft (22, 20 in FIG. 1) are axially displaced relative to each other, the cylindrical sleeve 140 and the jaw assembly 144 are similarly axially displaced relative to each other, from the positions shown in FIG. 5 to the positions shown in FIG. 6 and vice versa. It will also be appreciated that when the spool and shaft are in the approximate position shown in FIG. 1, the cylinder 140 and the jaw assembly 144 will be in the approximate position shown in FIG. 5; i.e., with the jaws open. Thus, those skilled in the art will further appreciate that when the spool is moved towards the thumb ring (24 in FIG. 1), or vice versa, the cylinder 140 and the jaw assembly 144 will be brought into the approximate position shown in FIG. 6 by movement of the jaw assembly into the cylinder, thereby closing the jaws.

In accord with the second embodiment of the invention, the cylinder 140 is provided with an annular stopping crimp 141 at a point distal of the distal end 116*a* of the coil 116, but proximal of the distal edge 142 of the cylinder 140. The distance between the stopping crimp 141 and the proximal end 152*a* of the jaw assembly is preferably approximately equal to the distance between the distal edge 142 of the cylinder 140 and the points 147*a*, 147*b* on the jaw cups where the distal edge of the cylinder lies when the jaws are closed. It will therefore be appreciated that when the jaws are brought into the closed position as shown in FIG. 6, the base member 152 of the jaw assembly 144 abuts the stopping crimp 141 in the cylinder 140 as soon as the jaws are closed. This prevents further movement of the cylinder 140 and jaw assembly 144 relative to each other and thereby limits the cutting force applied to the jaws.

Figure 7:
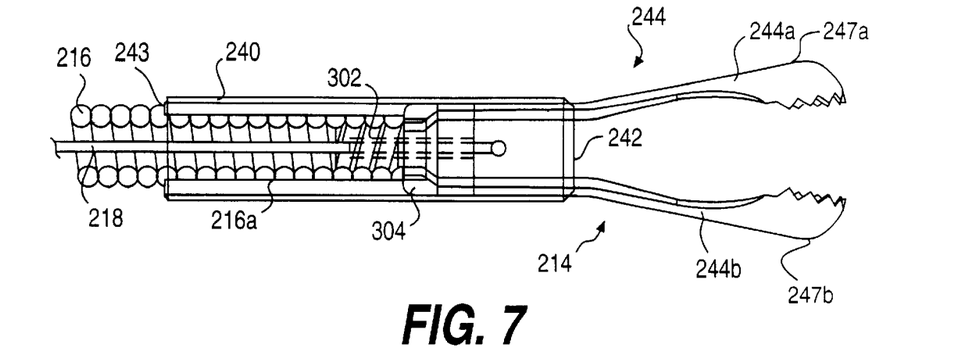
FIG. 7 is a view similar to FIG. 2 of a third embodiment of the invention.
Figure 8:
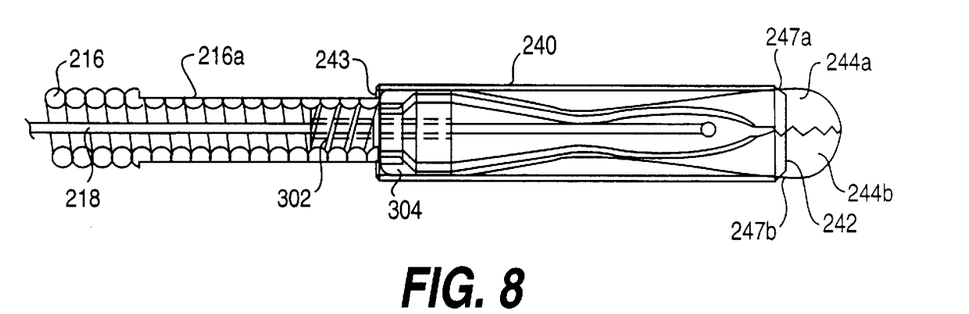
FIG. 8 is a view similar to FIG. 4 of the third embodiment of the invention.

Referring now to FIGS. 7 and 8, according to a third embodiment of the invention, the end effector 214 includes a cylinder 240 having a distal edge 242 and a jaw assembly 244. The jaw assembly 244 includes a pair of jaws 244*a*, 244*b*, a screw 302, and a washer or retaining sleeve 304. The jaw assembly is substantially the same the jaw assembly 44 described above with reference to FIGS. 2–4 and is coupled to the distal end of the coil 216 in substantially the same manner as described above. According to this embodiment, a portion 216*a* of the coil 216 which is proximally adjacent to the washer 304 is ground to a reduced external diameter. The length of the reduced diameter portion 216*a* is preferably approximately equal to the distance between the distal edge 242 of the cylinder 240 (when the jaws are open) and the points 247*a*, 247*b* on the jaw cups where the distal edge of the cylinder lies when the jaws are closed. In addition, the proximal end of the cylinder 240 is provided with a radially inward directed flange 243 which defines a proximal opening having a diameter slightly larger than the reduced diameter of the ground portion 216*a*. The cylinder 240 is coupled to the control wire 218 in substantially the same manner as the cylinder 40 of the first embodiment is coupled to the control wire 18, described above with reference to FIGS. 1–4. It will therefore be appreciated that when the jaws are brought into the closed position as shown in FIG. 8, the flange 243 of the cylinder 240 abuts the washer 304 as soon as the jaws are closed. This prevents further movement of the cylinder 240 and jaw assembly 244 relative to each other and thereby limits the cutting force applied to the jaws.

Figure 9:
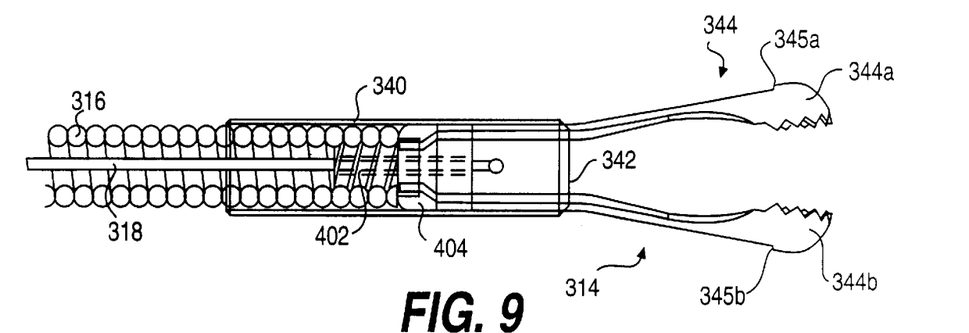
FIG. 9 is a view similar to FIG. 2 of a fourth embodiment of the invention.
Figure 10:
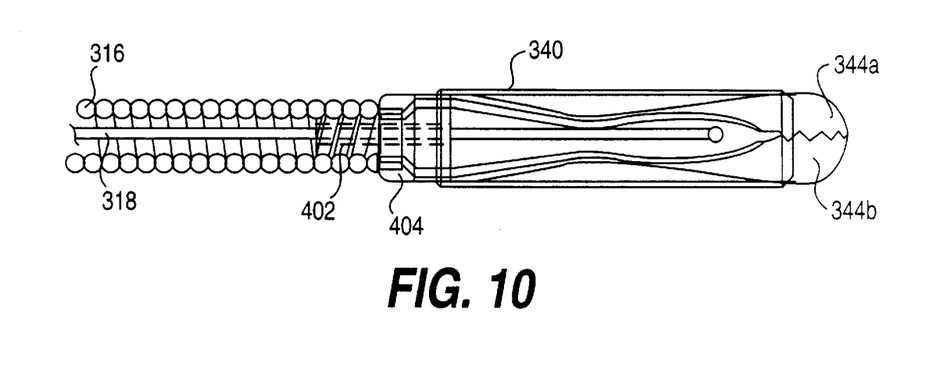
FIG. 10 is a view similar to FIG. 4 of the fourth embodiment of the invention.

Referring now to FIGS. 9 and 10, according to a fourth embodiment of the invention, the end effector 314 includes a cylinder 340 having a distal edge 342 and a jaw assembly 344. The cylinder 340 is substantially the same as the cylinder 40 described above and is coupled to the control wire 318 in substantially the same manner as the cylinder 40 is coupled to the wire 18. The jaw assembly 344 includes a pair of jaws 344*a*, 344*b*, a screw 402, and a washer or retaining sleeve 404. The jaw assembly is similar to the jaw assembly 44 described above with reference to FIGS. 2–4 and is coupled to the distal end of the coil 316 in substantially the same manner as described above. According to this fourth embodiment, each jaw 344*a*, 344*b* is provided with a outer surface step 345*a*, 345*b* which is located approximately at the points on the jaw cups where the distal edge of the cylinder lies when the jaws are closed. It will therefore be appreciated that when the jaws are brought into the closed position as shown in FIG. 10, the distal edge 342 of the cylinder 340 abuts the steps 345*a*, 345*b* on the outer surfaces of the jaws 344*a*, 344*b*. This prevents further movement of the cylinder 340 and jaw assembly 344 relative to each other and thereby limits the cutting force applied to the jaws.

There have been described and illustrated herein several embodiments of an endoscopic multiple sample bioptome. While particular embodiments of the invention have been described, it is not intended that the invention be limited thereto, as it is intended that the invention be as broad in scope as the art will allow and that the specification be read likewise. Thus, while particular configurations of the cutting edges of the jaws, it will be appreciated that other types of cutting edges could be utilized. In particular, the cutting edges may have teeth or a toothless sharp edge, or a combination of both. The teeth may be radially arranged or arranged in another manner. In addition, while the jaws have been shown as coupled to the coil with a screw and washer in several embodiments, other coupling means could be provided. Moreover, while the cylinder has been described as having a stopping crimp in the second embodiment, other types of radial occlusions may be used to limit movement of the jaw assembly and the cylinder relative to each other. In fact, if the base member of the jaw assembly and/or the cylinder is properly dimensioned and located, the coil itself can be used as the stopping device. It will therefore be appreciated that in the third embodiment of the invention, the proximal flange on the cylinder could be replaced with a stopping crimp. Also, it will be appreciated that while the invention was described as advantageously permitting the obtaining of multiple biopsies without removal from the surgical site, the apparatus of the invention, if desired, could still be used for obtaining single biopsies at a time. It will therefore be appreciated by those skilled in the art that yet other modifications could be made to the provided invention without deviating from its spirit and scope as so claimed.

We claim:

1. An endoscopic bioptome comprising:

an outer member having a proximal end and a distal end;

a control member having a proximal end and a distal end and extending through said channel;

a hollow member coupled to the distal end of said outer member;

a jaw assembly including resilient arms each having a distal end, the jaw assembly coupled to the distal end of said control member;

an actuating member coupled to the proximal end of said outer member and said control member for axially displacing said outer member and said control member relative to one another and extending said hollow member around said resilient arms so that the distal end of said resilient arms engage; and a displacement limiting member disposed at a distal end of the bioptome for limiting displacement of said hollow member relative to said jaw assembly, said hollow member including said displacement limiting member.

2. The endoscopic bioptome according to claim 1, wherein:

said jaw assembly includes a proximal base portion, and said displacement limiting member includes a radial occlusion on an interior of said hollow member which limits movement of said base portion of said jaw assembly relative to said hollow member.

3. The endoscopic bioptome according to claim 2, wherein:

said radial occlusion is an annular crimp.

4. An endoscopic bioptome comprising:

an outer member having a proximal end and a distal end;

a control member having a proximal end and a distal end and extending through said channel;

a hollow member coupled to the distal end of said control member;

a jaw assembly including resilient arms each having a distal end, the jaw assembly coupled to the distal end of said outer member;

an actuating member coupled to the proximal end of said outer member and said control member for axially displacing said outer member and said control member relative to one another and extending said hollow member around said resilient arms so that the distal end of said resilient arms engage; and a displacement limiting member disposed at a distal end of the bioptome for limiting displacement of said hollow member relative to said jaw assembly, said hollow member including said displacement limiting member.

5. The endoscopic bioptome according to claim 4, wherein:

said outer member has a reduced diameter distal portion, said jaw assembly includes a base portion which couples said jaw assembly to said outer member, said base portion having an outer diameter which is larger than said reduced diameter, and said displacement limiting member includes a radially inward protrusion on said hollow member which limits the movement of said hollow member in relation to said base portion.

6. The endoscopic bioptome according to claim 5, wherein: said radially inward protrusion is located a first distance from said base member, said hollow member has a distal edge located a second distance from said jaw cups, and said first distance is substantially equal to said second distance.

7. The endoscopic bioptome according to claim 5, wherein:

said radially inward protrusion is a proximal flange.

8. An endoscopic bioptome comprising:

an outer member having a proximal end and a distal end;

a control member having a proximal end and a distal end and extending through said channel;

a hollow member coupled to the distal end of said control member;

a jaw assembly including resilient arms each having a distal end, the jaw assembly coupled to the distal end of said outer member;

an actuating member coupled to the proximal end of said outer member and said control member for axially displacing said outer member and said control member relative to one another and extending said hollow member around said resilient arms so that the distal end of said resilient arms engage; and a displacement limiting member disposed at a distal end of the bioptome for limiting displacement of said hollow member relative to said jaw assembly, said jaw assembly including said displacement limiting member.

9. The endoscopic bioptome according to claim 8, wherein:

said displacement limiting member includes a surface step on an outer surface of the distal end of at least one of said resilient arms.

10. The endoscopic bioptome according to claim 9, wherein:

said displacement limiting member includes a surface step on an outer surface of the distal end of each of said resilient arms.

11. An endoscopic bioptome comprising:

an outer member having a proximal end and a distal end;

a control member having a proximal end and a distal end and extending through said channel;

a hollow member coupled to the distal end of one of said outer member and said control member;

a jaw assembly including resilient arms each having a distal end, the jaw assembly coupled to the distal end of one of said outer member and said control member;

an actuating member coupled to the proximal end of said outer member and said control member for axially displacing said outer member and said control member relative to one another and extending said hollow member around said resilient arms so that the distal end of said resilient arms engage; and a displacement limiting member disposed at a distal end of the bioptome for limiting displacement of said hollow member relative to said jaw assembly, said displacement limiting member including a surface step on an outer surface of the distal end of at least one of said resilient arms.

\* \* \* \* \*

UNITED STATES PATENT AND TRADEMARK OFFICE
CERTIFICATE OF CORRECTION

PATENT NO. : 6,461,310 B1
DATED : October 8, 2002
INVENTOR(S) : Matthew A. Palmer et al.

It is certified that error appears in the above-identified patent and that said Letters Patent is hereby corrected as shown below:

<u>Title page,</u>
Under Item [76], Inventors, insert
-- (73) Assignee: Symbiosis Corporation, Miami, FL (US) --.

Item [62], Related U.S. Application Data, should read as follows:

-- Division of application No. 08/960,214, filed on Oct. 29, 1997, Pat. No. 6,123,678, which is a continuation of application No. 08/641,805, filed on May 2, 1996, Pat. No. 5,797,957. --

Signed and Sealed this

Thirty-first Day of December, 2002

JAMES E. ROGAN
*Director of the United States Patent and Trademark Office*